(12) United States Patent
Machit et al.

(10) Patent No.: US 7,226,420 B2
(45) Date of Patent: Jun. 5, 2007

(54) CUFF VOLUME CONSTRAINING DEVICE

(75) Inventors: Denize Marie Machit, Valley Village, CA (US); Gregory Randolph Alkire, Newbury Park, CA (US)

(73) Assignee: Pronk Technologies Inc., South Pasadena, CA (US)

( * ) Notice: Subject to any disclaimer, the term of this patent is extended or adjusted under 35 U.S.C. 154(b) by 0 days.

(21) Appl. No.: 11/164,652

(22) Filed: Nov. 30, 2005

(65) Prior Publication Data
US 2006/0122518 A1  Jun. 8, 2006

Related U.S. Application Data

(60) Provisional application No. 60/633,352, filed on Dec. 3, 2004.

(51) Int. Cl.
*A61B 5/00* (2006.01)
*G09B 23/28* (2006.01)

(52) U.S. Cl. .................. 600/490; 434/262; 434/268

(58) Field of Classification Search ................ None
See application file for complete search history.

(56) References Cited

U.S. PATENT DOCUMENTS

| 3,906,937 | A | * | 9/1975 | Aronson | ............... 600/493 |
|---|---|---|---|---|---|
| 4,464,123 | A | * | 8/1984 | Glover et al. | ............... 434/268 |
| 4,716,906 | A | | 1/1988 | Ruff | |
| 5,016,466 | A | | 5/1991 | Ness et al. | |
| 5,027,641 | A | | 7/1991 | Costello, Jr. | |
| 5,570,694 | A | | 11/1996 | Rometsch | |
| 5,800,359 | A | | 9/1998 | Medero et al. | |
| 2004/0094674 | A1 | | 5/2004 | Bozmoski et al. | |
| 2004/0101814 | A1 | | 5/2004 | Morris et al. | |

* cited by examiner

*Primary Examiner*—Robert L. Nasser
(74) *Attorney, Agent, or Firm*—Michael Blaine Brooks, P.C.; Michael B. Brooks; Rosemarie F. Jones (57) ABSTRACT

A system, method, and apparatus for testing a non-invasive blood pressure measurement device wherein a blood pressure monitor, a blood pressure cuff, and a blood pressure simulator are pneumatically connected and the blood pressure cuff is inserted into the aperture of an expansion-limiting or cuff volume constraining element. A cuff volume constraining device is made of flexible material having one or more apertures for constraining cuff volume during cuff expansion during blood pressure measurement device testing.

21 Claims, 8 Drawing Sheets

CUFF VOLUME CONSTRAINING DEVICE

CROSS-REFERENCE TO RELATED APPLICATION

This application claims the benefit of U.S. Provisional Patent Application Ser. No. 60/633,352 filed Dec. 3, 2004, entitled "CUFF VOLUME CONTROLLING DEVICE," which is hereby incorporated by reference herein for all purposes.

BACKGROUND

This invention relates to non-invasive blood pressure monitoring devices, systems, and methods and more particularly to systems, methods, and devices for volumetrically constraining blood pressure cuffs. Non-invasive blood pressure ("NIBP") monitors typically require periodic testing to validate whether they are operating correctly. This requirement may be met by using a simulator to generate pressure signals that approximate those created by a patient's arm in surface contact with a blood pressure cuff. In some applications of a simulator to an NIBP, the cuff may wrap on itself, which may result in a larger than ideal volume. The accuracy of the pressure pulse simulation is enhanced if the cuff volume is constrained to approximately match the volume it would otherwise displace if applied to an actual patient's arm. One attempt at constraining the expansion of the cuff in a simulated condition has the cuff wrapped around a rigid article often termed a mandrel and having a diameter of the average or typical patient's arm. When a mandrel is used to simulate the geometry of the average or typical patient's arm, the cuff is wrapped around the mandrel such that a surface of the cuff contacts the mandrel in the same manner as it would a patient's arm.

SUMMARY OF THE INVENTION

An exemplary embodiment of the present invention includes a system for testing a non-invasive blood pressure measurement device, wherein the blood pressure measurement device includes a blood pressure monitor and a blood pressure cuff. The system includes a blood pressure simulator adapted to be pneumatically connected to the blood pressure cuff and blood pressure monitor; and a cuff volume constraining element that comprises at least one hollow member adapted to receive the blood pressure cuff.

Another exemplary embodiment of the present invention includes a system for testing a non-invasive blood pressure measurement device. This system includes a blood pressure monitor, a blood pressure cuff, a blood pressure simulator, and a cuff volume constraining element that comprises at least one hollow member. The blood pressure monitor, the blood pressure cuff, and the blood pressure simulator are pneumatically connected during testing and the blood pressure cuff is placed inside a cuff volume area in the at least one hollow member as a and thereby limit the maximal diameter and maximal volume to which the blood pressure cuff may expand during testing.

Another exemplary embodiment of the invention includes a method for testing a non-invasive blood pressure measurement device pneumatically connected to a blood pressure cuff, a blood pressure simulator, and a blood pressure monitor. The method includes the steps of placing the blood pressure cuff into a volume cuff area or aperture of the cuff constraining device having at least one hollow member so as to limit the maximal diameter and maximal volume to which the blood pressure cuff may expand during testing; and pneumatically expanding the blood pressure cuff while the blood pressure simulator simulates a test subject.

Another exemplary embodiment of the invention is an apparatus having an aperture for receiving a blood pressure cuff and constraining the volumetric expansion of the blood pressure cuff while testing a pneumatically coupled non-invasive blood pressure measurement device. The exemplary apparatus further comprises at least one sheet of flexible and substantially inelastic material connected at a first longitudinal end to a second longitudinal end.

BRIEF DESCRIPTION OF THE DRAWINGS

For a more complete understanding of the present invention and for further features and advantages, reference is now made to the following description taken in conjunction with the accompanying drawings, in which.

DETAILED DESCRIPTION

The present invention in its several embodiments includes a device for constraining cuff volume during NIBP simulation. Some exemplary embodiments of the cuff volume constraining device or element comprise a flexible inelastic hollow cylindrical member which is placed outside the outer surface of a blood pressure cuff. The blood pressure cuff is connected pneumatically to a blood pressure simulator and a blood pressure monitor. During operation, the blood pressure cuff inflates inside or within the constraining bounds of the cuff volume constraining device until the outside diameter of the blood pressure cuff matches the inside diameter of the cuff volume constraining device. This limits the volume of the blood pressure cuff to the volume of the cuff volume constraining device. When not in operation, the cuff volume constraining device, which may be a flexible inelastic hollow cylindrical member, may be folded or rolled for compact storage. Other mechanisms to facilitate portability, such as crumpling the cuff volume constraining device to fit into a small space, may also be done.

In an exemplary embodiment, the cuff volume constraining device may be made of a sheet of flexible material nylon fabric, which may be rolled or folded to fit in compact spaces, the sheet of flexible material may be fixedly attached to itself, for example by bringing the two ends in layered proximity and creating a seam, via stitching, fusing, or an adhesive for example, to form a tube or a cylinder. This sheet of material may include a number of pieces to form the sheet of flexible material and the sheet may be made of a substantially inelastic material. The sheet of flexible material may be inelastic or substantially inelastic so that it may not be stretched or not substantially stretched to extend its dimensions when under pressure from the expanding cuff. In an exemplary embodiment of the cuff volume constraining device, a flexible inelastic hollow cylindrical member constrains the blood pressure cuff volume to less than approximately 350 ml. In other exemplary embodiments of the cuff volume constraining device, a flexible inelastic hollow cylindrical member may constrain the volume of the blood pressure cuff to be a volume in the range of 10 ml to 1000 ml or less than 1000 ml. In another exemplary embodiment, of the cuff volume constraining device may comprise of two or more hollow members that may be fashioned via a second seam across the width of an already folded member, for example.

Figure 1:
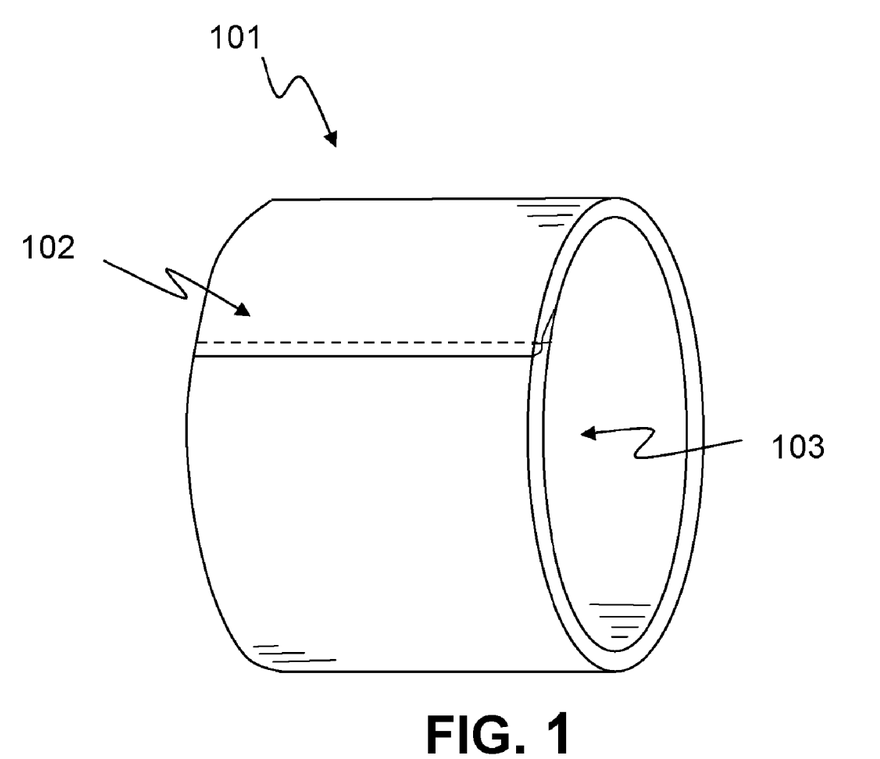
FIG. 1 is a perspective view of an exemplary cuff constraining device, according to an exemplary embodiment of the invention.

FIG. 1 illustrates an exemplary embodiment of cuff volume constraining device 101 that may be manufactured of a flexible but inelastic material that is organic or inorganic, such as, but not limited to, silicon, rubber, plastic, silk or nylon fabric or other fabrics of natural or man-made fibers. The material or sheet of material may be fixedly attached to itself along a seam 102, for example, using stitches. A blood pressure cuff may be placed or inserted inside the formed cuff volume 103.

Figure 2:
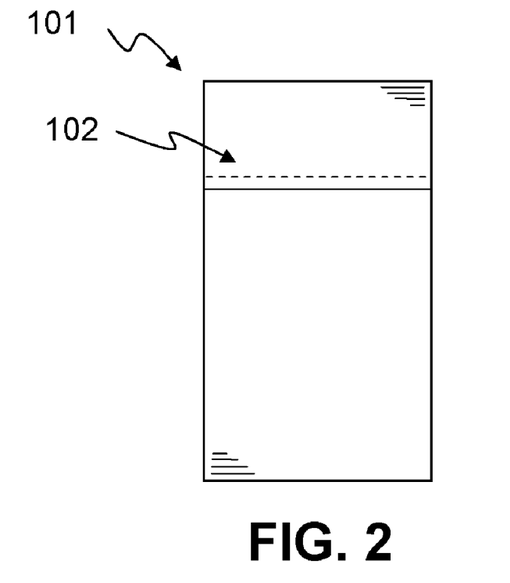
FIG. 2 is a front view of the exemplary cuff constraining device, according to an exemplary embodiment of the invention.

FIG. 2 illustrates in a front view an exemplary embodiment of the cuff volume constraining device 101 showing the seam 102 where the material is fixedly attached to itself. In some embodiments, the cylindrical member is made from a sheet of material that may be a fabric of fiber, e.g., nylon, having a length longer than its width. The sheet may be looped around in length with the two longitudinal ends sewn together, for example, by multiple stitches, thereby forming the hollow cylindrical or tubular member. In some embodiments, the exemplary fabric may be nylon that may be tightly- or loosely-woven nylon, including ballistic nylon and non-rip nylon. In other embodiments, the sheet or fabric may comprise flexible and substantially inelastic nylon or other materials such as silk in a satin fabric.

Figure 3:
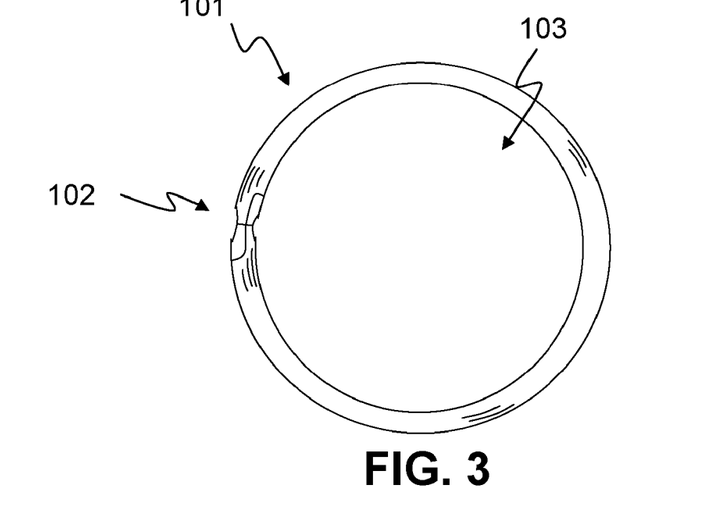
FIG. 3 is a side view of the exemplary cuff constraining device, according to an exemplary embodiment of the invention.

In some embodiments, the cuff volume constraining device may be made from a sheet of material that includes a number of pieces. For example, the constraining device 101 may be made by two or more pieces of nylon sewn together thereby having multiple seams and forming the hollow cylindrical member. In some other embodiments, the sheet of material may be made by one or more materials, for example, nylon and strong cloth fabric. FIG. 3 illustrates in a side view the cuff volume constraining device 101 showing the seam 102. The blood pressure cuff is typically placed inside the cuff volume area 103.

Figure 4A:
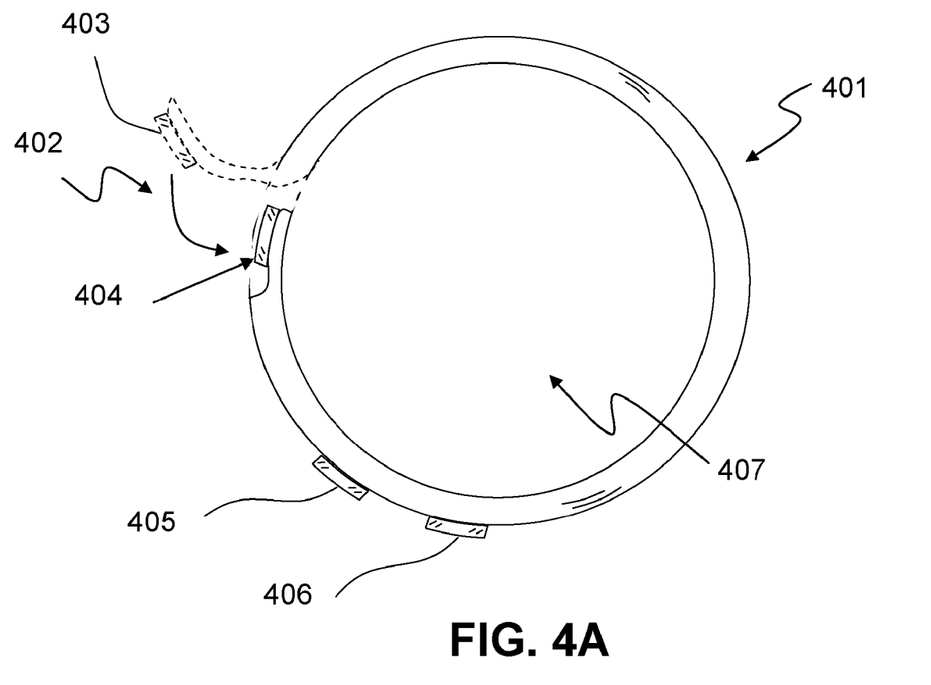
FIG. 4A is a side view of an exemplary cuff constraining device; according to an another exemplary embodiment of the invention.
Figure 4B:
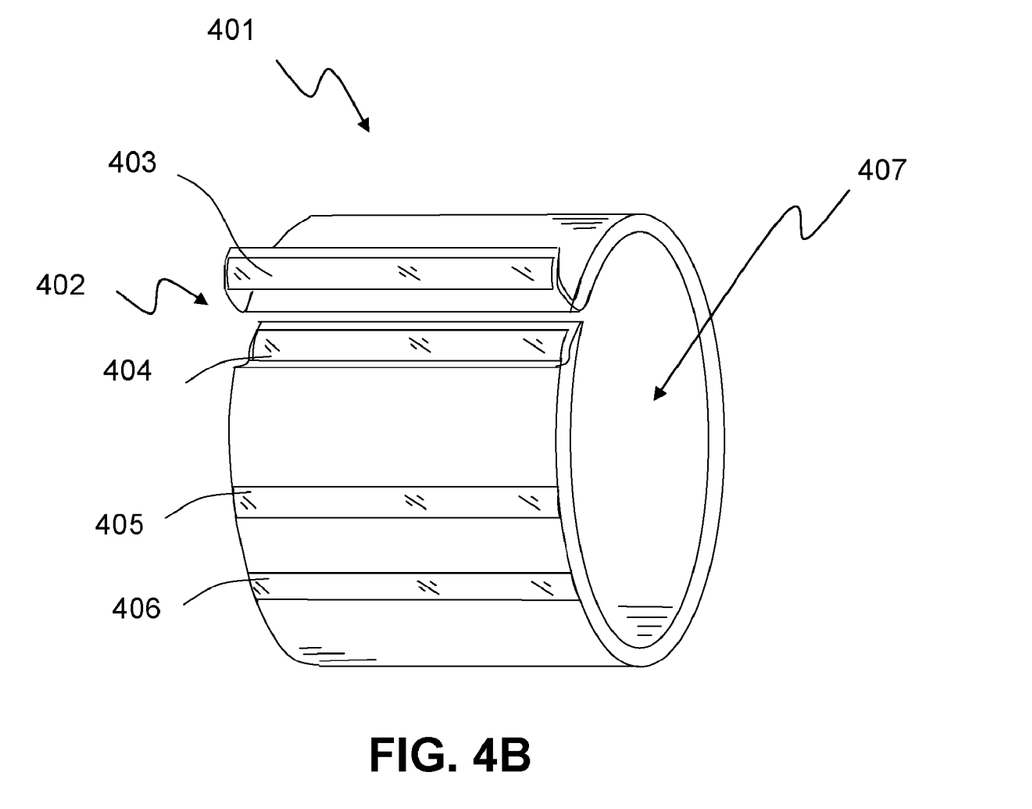
FIG. 4B is a perspective view of the exemplary cuff constraining device, according to an exemplary embodiment of the invention.

In other embodiments, the exemplary cuff volume constraining device 401 of FIG. 4A comprises a sheet of flexible material which may be detachably attached to itself along a seam. Examples of detachable attachment include, but are not limited to hook-and-loop members, snaps, zippers, laces, hook and loop such as VELCRO™, or other detachable means of attachment or attachments/detachment devices that are themselves fixedly attached to the longitudinal ends of the sheet of material from which the cuff volume constraining device may be manufactured. The exemplary means of attachment or attachments/detachment devices allow the longitudinal ends of the cuff constraining device to be fastened together to form a hollow cylinder or tube by which it may receive and constrain an expandable blood pressure cuff. In this exemplary embodiment, the detachable fastening means or attachments/detachment devices may be fixedly attached at a plurality of locations longitudinally along the flexible material such that the cuff volume constraining device may set at two or more diameters and may thereby constrain the blood pressure cuff to one of a plurality of pre-set volumes. FIG. 4A illustrates, in a side view, an exemplary embodiment of the cuff volume constraining device 401 where the longitudinal ends of the cuff volume constraining device 401 may be detachably attached at a detachable seam 402. This exemplary embodiment further includes two additional detachable attachment regions 405, 406. An exemplary embodiment of attachments/detachment device or means of detachable attachment may be a two-part hook and loop member, and other examples of detachable attachment include, but are not limited to: snaps, laces, and zippers. Additional exemplary detachable attachment regions or sites 405, 406 allow the volume and diameter of the cuff volume constraining device 401 to be adjusted to pre-determined diameters. The blood pressure cuff is typically inserted inside the cuff volume area 407 prior to expansion as part of a simulation. This exemplary embodiment may be made of nylon and made with a number of flexible, typically inelastic, materials and/or pieces of materials. FIG. 4B illustrates a perspective view of the exemplary embodiment of the cuff volume constraining 401 of FIG. 4A showing three detachable attachment sites or regions 404-406 that when brought into contact with the complementary region 403, may form one of three pre-set diameters, or looped longitudinal lengths, for volumetric cuff constraint.

Figure 5A:
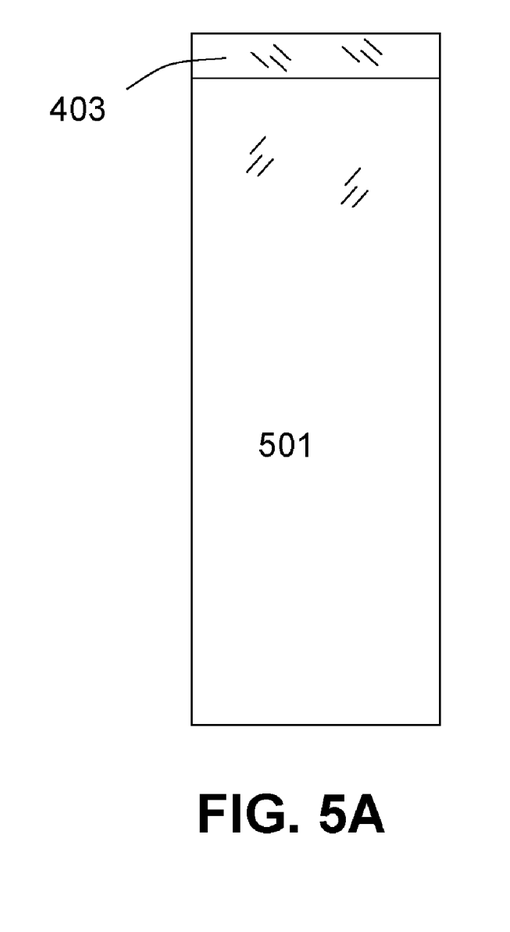
FIG. 5A is a top plan view of the exemplary cuff constraining device, according to an exemplary embodiment of the invention.
Figure 5B:
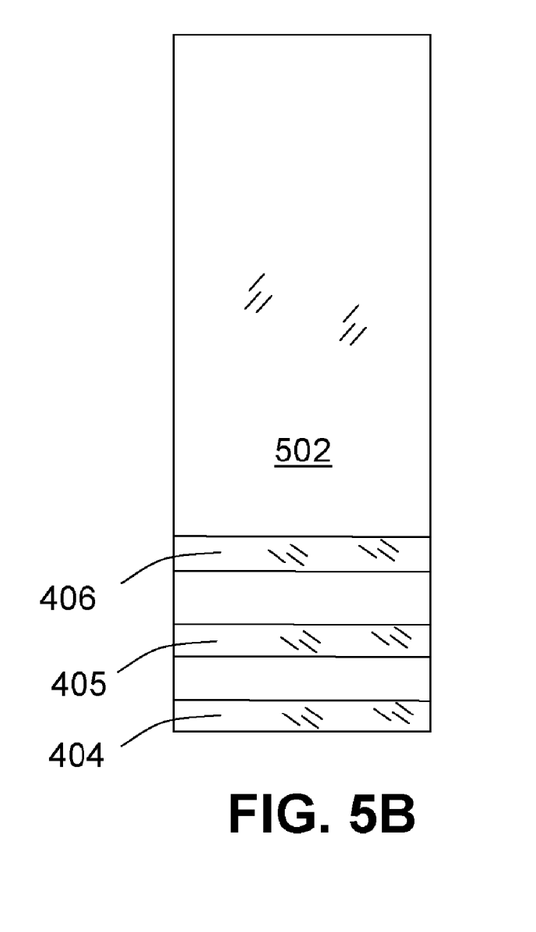
FIG. 5B is a bottom plan view of the exemplary cuff constraining device, according to an exemplary embodiment of the invention.

FIG. 5A is a top plan view of the exemplary embodiment of the cuff volume constraining device 401 of FIG. 4A, unrolled to illustrate the exemplary device having a first surface 501 that, when the cuff volume constraining device 401 is detachably attached at the seam 402, is the inward or cuff facing surface of the cuff volume constraining device 401. A first attachments/detachment device portion 403 such as the hook or loop portion of a hook and look device may be located at a first longitudinal end of the cuff volume constraining device 401. FIG. 5B is a bottom plan view of the exemplary embodiment of the cuff volume constraining device 401 of FIG. 5A, unrolled to illustrate a second surface 502 that, when the cuff volume constraining device 401 is detachably attached at the seam 402, is the outward facing surface of the cuff volume constraining device 401. A second attachments/detachment device portion 404 such as the hook or loop portion of a hook and look device may be located at a second longitudinal end of the cuff volume constraining device 401. Additional detachable attachment sites 405, 406 are shown at intermediate points along on the exemplary cuff volume constraining device 401.

Figure 6A:
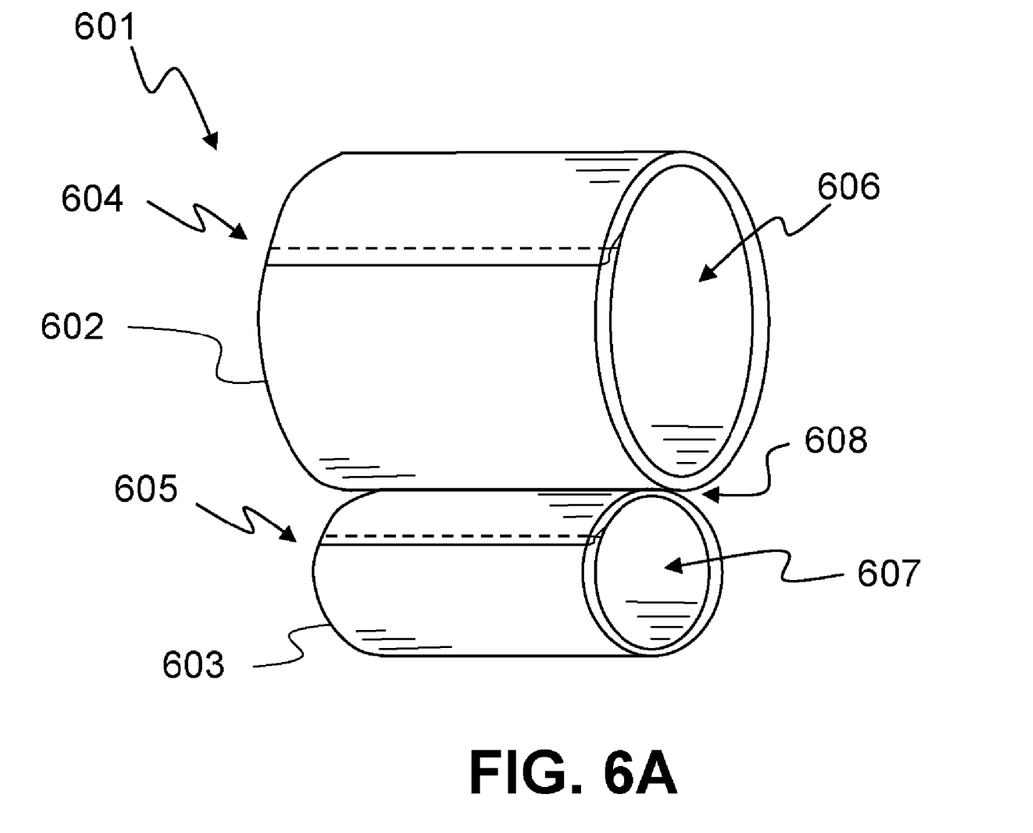
FIG. 6A is a perspective view of an exemplary h cuff constraining device, according to an exemplary embodiment of the invention.
Figure 6B:
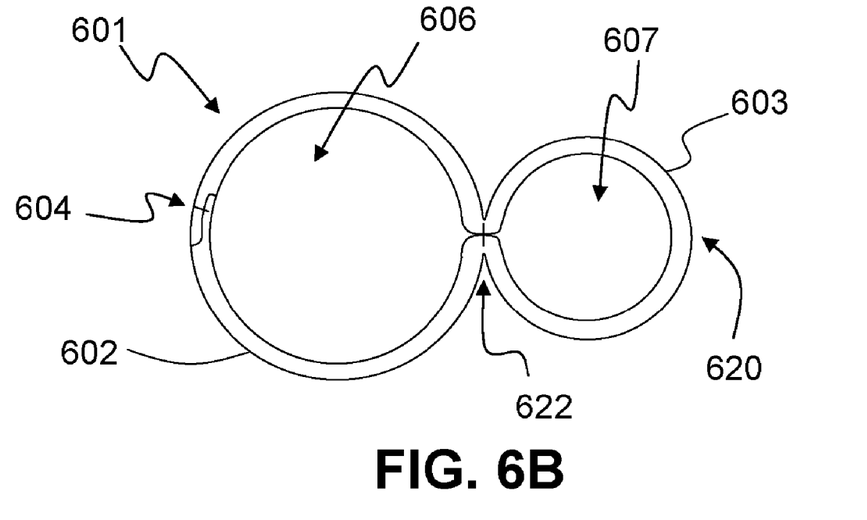
FIG. 6B is a side view of the exemplary cuff constraining device, according to an exemplary embodiment of the invention.
Figure 6C:
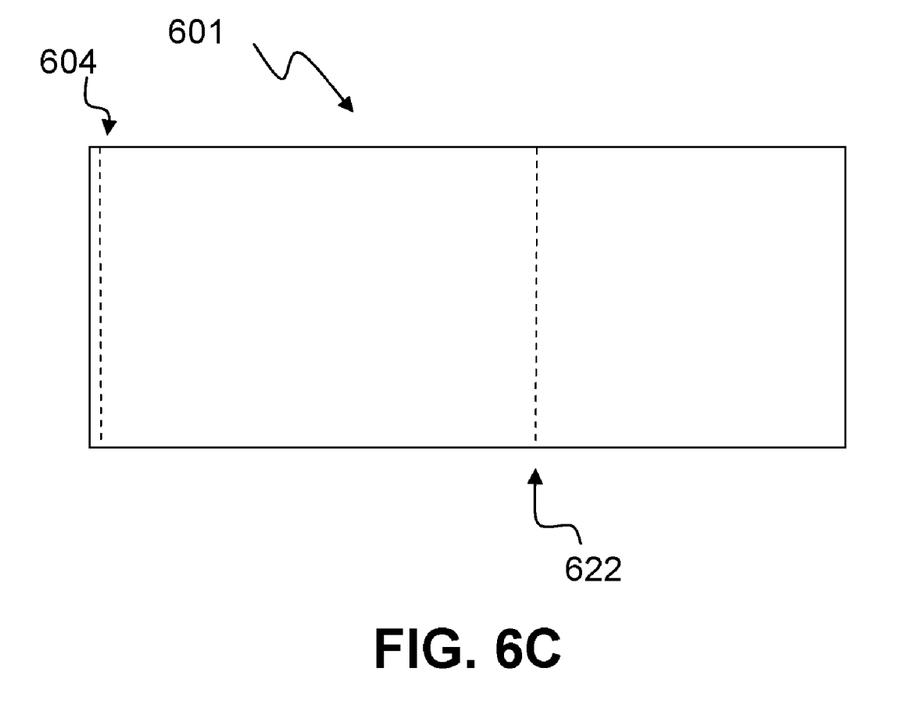
FIG. 6C is a top view of the exemplary cuff constraining device, according to an exemplary embodiment of the invention.

FIG. 6A is a perspective view of an exemplary embodiment of the cuff volume constraining device 601 manufactured of a flexible inelastic material comprising a first hollow member 602 and a second hollow member 603, both being adapted in this example by way of their respective tubular apertures 606, 607 to receive a blood pressure cuff. The material may be fixedly attached to itself along one or more seams 604, 605 via, for example, stitches. This exemplary embodiment of the cuff volume constraining device 601 is thus able to constrain blood pressure cuffs across two ranges of volumes. For example, a first chamber or cuff volume constraining aperture 606 may dimensioned to constrain a blood pressure cuff to approximately 100 ml and the second cuff volume constraining aperture 607 may be dimensioned to constrain a blood pressure cuff to approximately 400 ml. This constraining device 601 is thus able to support the simulation and test for at least two volumetric ranges of cuff expansion, for example, to constrain the blood pressure cuff to a volume applicable or otherwise suitable for toddlers or small children 607, and the other cuff volume area suitable for adults 607. Other variations of the constraining device may also be created, such as a device having more than two hollow members 602, 603 each sized or adapted to constrain cuffs to differing pre-set volumes. These hollow members may be connected in various ways along a line or region 608, for example, sewn together, attached by ties or cords, by hook and loop attachments such VELCRO®, and the like and may be made by stitches interposed between a longitudinal stitch line and the fold of an otherwise one-piece looped fabric, for example. FIG. 6B is a side view of an exemplary embodiment of the cuff volume constraining device showing a rounded fold 620 on one side of the device and a seam 604 opposite the side of the rounded fold 620 where an interposed stitch line 622 supports the second cuff volume constraining aperture 607 and where the interposed stitch 622 along with a stitched seam 604 support the first cuff volume constraining aperture 606. FIG. 6C is a top view of the exemplary embodiment of the cuff volume constraining device illustrating exemplary stitch lines 604, 622.

Figure 7A:
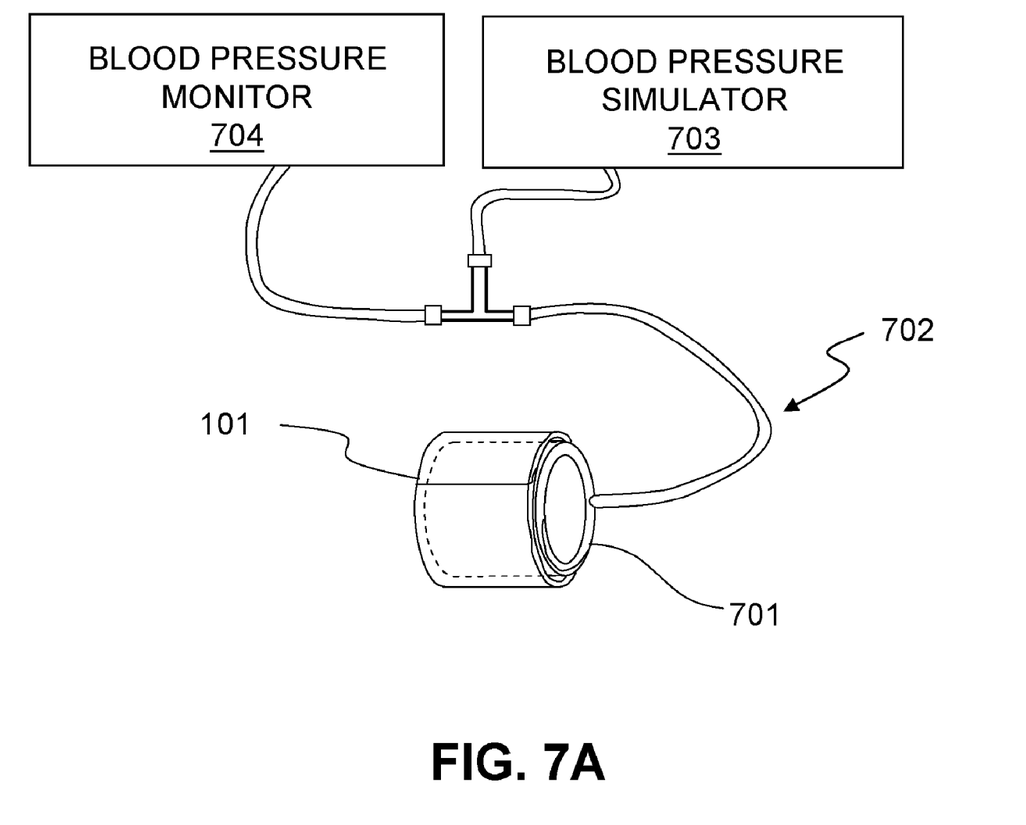
FIG. 7A is an exemplary diagram of the cuff constraining device and a non-invasive blood pressure measurement device, according to an exemplary embodiment of the invention.
Figure 7B:
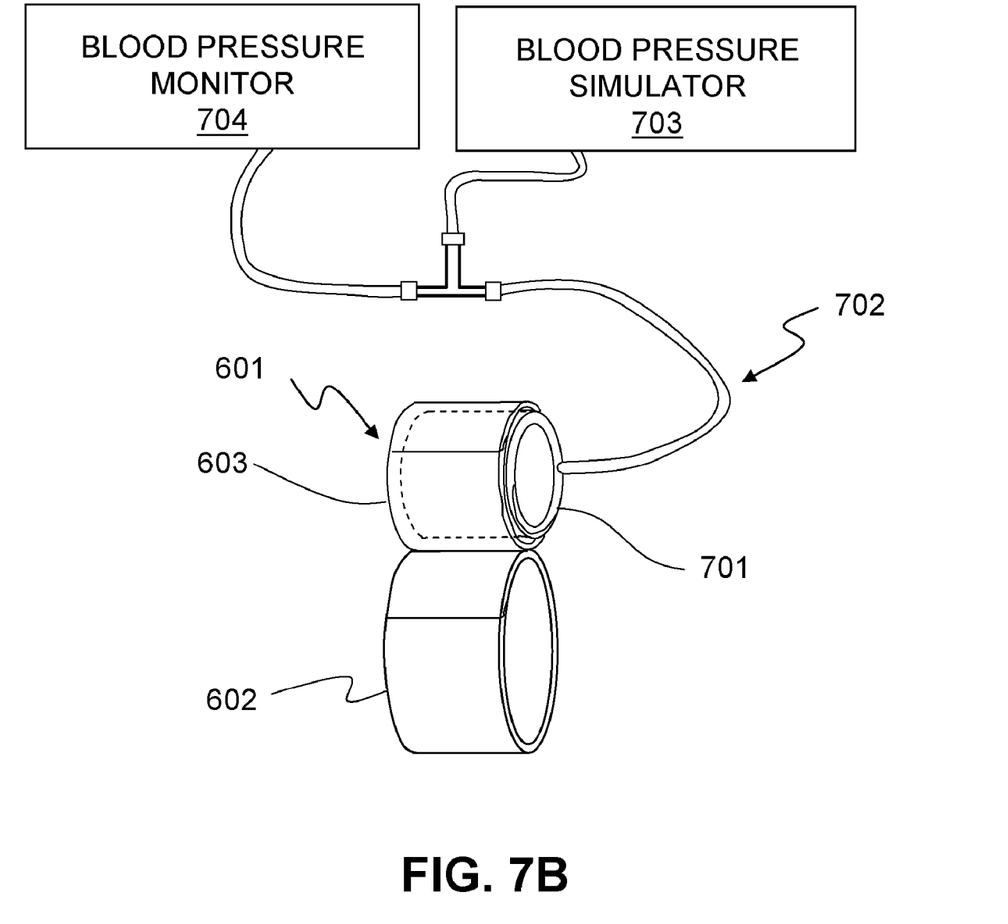
FIG. 7B is an exemplary diagram of the cuff constraining device and a non-invasive blood pressure measurement device, according to an exemplary embodiment of the invention.

FIG. 7A is a diagram of the cuff volume constraining device 101 as it may be deployed in testing a non-invasive blood pressure measurement device where the cuff volume constraining device 101 is positioned about the blood pressure cuff 701 which is pneumatically connected via a tube 702 to a blood pressure simulator 703 and a blood pressure monitor 704. Typically, the blood pressure cuff is inserted into the constraining device 101. The simulator 703 typically generates pressure signals that approximate those created by a patient's arm in surface contact with a blood pressure cuff where the pulses are measured by the blood pressure monitor 704 having its cuff volumetrically constrained by the exemplary cuff volume constraining device 101. FIG. 7B is a diagram of the cuff volume constraining device 601 as it may be used in testing a non-invasive blood pressure measurement device where a portion of the cuff volume constraining device 601 is positioned about the blood pressure cuff 701 which is pneumatically connected via a tube 702 to a blood pressure simulator 703 and a blood pressure monitor 704. Typically, the blood pressure cuff is inserted into one of the hollow members of differing diameters when expanded, i.e., in this exemplary embodiment either the first, or larger, hollow member 602 or the second, or smaller, hollow member 603, and in FIG. 7B is shown inserted into the second, or smaller, hollow member 603 of the cuff volume constraining device 601.

The embodiments of the cuff volume constraining device shown in the various figures are for illustration purposes. Variations on the shape of the cuff volume constraining device may also be implemented, for example, having a constraining device that is hexagonal, octagonal, or any polygonal shape. This shape may be obtained before and/or even after the blood pressure cuff placed inside or inserted into the cuff volume area of the constraining device and inflated or expanded. One of ordinary skill in the art will also realize that the hollow member may be made in many ways, so that a cuff volume area is created thereby constraining the expansion of a blood pressure cuff. Furthermore, in some embodiments, the cuff volume constraining device may be enclosed in one end, for example, forming a cup-like device wherein a blood pressure cuff may still be inserted into the open end or into the cuff volume area of the constraining device. Other flexible and inelastic materials may also be used.

Many alterations and modifications may be made by those having ordinary skill in the art without departing from the spirit and scope of the invention. Therefore, it must be understood that the illustrated embodiments have been set forth only for the purposes of example and that it should not be taken as limiting the invention as defined by the following claims.

The definitions of the words or elements of the following claims are, therefore, defined in this specification to include not only the combination of elements which are literally set forth, but all equivalent structure, material or acts for performing substantially the same function in substantially the same way to obtain substantially the same result. In addition to the equivalents of the claimed elements, obvious substitutions now or later known to one with ordinary skill in the art are defined to be within the scope of the defined elements.

What is claimed is:

1. A system for testing a non-invasive blood pressure measurement device, wherein the blood pressure measurement device includes a blood pressure monitor and a blood pressure cuff, the system comprising:
   the blood pressure monitor and the blood pressure cuff;
   a blood pressure simulator adapted to pneumatically connect to the blood pressure cuff and blood pressure monitor; and
   at least one hollow member adapted to receive and volumetrically constrain the blood pressure cuff.

2. The system of claim 1, wherein the at least one hollow member is tubular.

3. The system of claim 1, wherein the at least one hollow member is cylindrical.

4. The system of claim 1, wherein the at least one hollow member comprises two connected hollow members.

5. The system of claim 4, wherein a first connected hollow member of the two connected hollow members limits the blood pressure cuff to a volume less than approximately 400 ml and a second connected hollow member of the two connected hollow members limits the blood pressure cuff to a volume less than approximately 100 ml.

6. The system of claim 1, wherein the at least one hollow member is flexible and substantially inelastic.

7. The system of claim 1, wherein the at least one hollow member limits the maximum diameter and volume to which the blood pressure cuff may expand.

8. The system of claim 1, wherein the at least one hollow member comprises at least one sheet of flexible and substantially inelastic material having a first longitudinal end and a second longitudinal end wherein the first longitudinal end and the second longitudinal end are attached.

9. The apparatus of claim 8, wherein the at least one hollow member further comprises a second hollow member adapted to receive a second blood pressure cuff in a second cuff volume area and to limit the maximal diameter and to limit the maximal volume to which the second cuff may expand, and wherein the second hollow member is supported by a region of attachment between two portions of the least one sheet of flexible and substantially inelastic material.

10. The apparatus of claim 8, wherein a first hollow member of the at least one hollow member limits the blood pressure cuff to a volume less than approximately 100 ml and a second hollow member of the at least one hollow member limits the blood pressure cuff to a volume less than approximately 400 ml.

11. A system for testing a non-invasive blood pressure measurement device comprising:
a blood pressure monitor;
a blood pressure cuff;
a blood pressure simulator; and
at least one hollow member having an aperture adapted to limit the maximal diameter and the maximal volume to which the blood pressure cuff may expand during testing; and
wherein the blood pressure monitor, the blood pressure cuff, and the blood pressure simulator are pneumatically connected during testing and the blood pressure cuff is placed inside the aperture of the at least one hollow member.

12. The system of claim 11, wherein the at least one hollow member is tubular.

13. The system of claim 11, wherein the at least one hollow member is cylindrical.

14. The system of claim 11, wherein the at least one hollow member is flexible and inelastic.

15. The system of claim 11, wherein the at least one hollow member comprises at least one sheet of flexible and substantially inelastic material having a first longitudinal end and a second longitudinal end wherein the first longitudinal end and the second longitudinal end are attached.

16. The system of claim 15, wherein the at least one hollow member further comprises a second hollow member adapted to receive a second blood pressure cuff in a second cuff volume area and to limit the maximal diameter and to limit the maximal volume to which the second cuff may expand, and wherein the second hollow member is supported by a region of attachment between two portions of the least one sheet of flexible and substantially inelastic material.

17. The apparatus of claim 15, wherein a first hollow member of the at least one hollow member limits the blood pressure cuff to a volume less than approximately 100 ml and a second hollow member of the at least one hollow member limits the blood pressure cuff to a volume less than approximately 400 ml.

18. A method for testing a non-invasive blood pressure measurement device pneumatically connected to a blood pressure cuff, a blood pressure simulator, and a blood pressure monitor, the method comprising the steps of:
placing the blood pressure cuff into an aperture of cuff volume constraining element wherein the cuff volume constraining element is adapted to limit the diameter and volume to which the blood pressure cuff may expand during testing; and
pneumatically expanding the blood pressure cuff while the blood pressure simulator simulates a test subject.

19. The method of claim 18, wherein the cuff volume constraining element comprises two connected hollow members.

20. The method of claim 18, wherein the step of placing the blood pressure cuff into an aperture of cuff volume constraining element wherein the cuff volume constraining element is adapted to limit the diameter and volume to which the blood pressure cuff may expand during testing.

21. The method of claim 18, wherein the step placing the blood pressure cuff into an aperture of cuff volume constraining element includes the step of forming the aperture about the blood pressure cuff via a detachable seam.

* * * * *